United States Patent [19]

Fujiwara et al.

[11] 4,404,409
[45] * Sep. 13, 1983

[54] PROCESS FOR PREPARING METHYL TERTIARY-BUTYL ETHER

[75] Inventors: Yasuo Fujiwara, Tokyo; Tetsuya Takezono, Kawasaki, both of Japan

[73] Assignee: Nippon Oil Co., Ltd., Japan

[*] Notice: The portion of the term of this patent subsequent to Jan. 8, 1997, has been disclaimed.

[21] Appl. No.: 125,655

[22] Filed: Feb. 28, 1980

[30] Foreign Application Priority Data

Mar. 5, 1979 [JP] Japan .................................. 54-25349

[51] Int. Cl.³ ...................... C07C 41/00; C07C 41/06
[52] U.S. Cl. .................................................... 568/697
[58] Field of Search ......................................... 568/697

[56] References Cited

U.S. PATENT DOCUMENTS 4,182,913  1/1980  Takezono et al. ................... 568/697
4,267,393  5/1981  Torck et al. ......................... 568/697

Primary Examiner—Howard T. Mars
Attorney, Agent, or Firm—Ostrolenk, Faber, Gerb & Soffen

[57] ABSTRACT

A process for continuously preparing methyl tertiary-butyl ether with high yield involves reacting an isobutylene-containing/hydrocarbon and methanol by continuously passing the isobutylene and methanol, in a molar ratio of isobutylene to methanol of 1 to 0.6–1.4 at a temperature of 60°–100° C. at a liquid space velocity of 0.1–50 1/hour and at a pressure of 1–50 atmospheres, through a first reactor filled with strong acid type cation exchange resin particles having an average particle diameter of 0.2–10 mm; dividing the mixture of the reaction products in two streams, the flow rate of the first stream being 3–15 times the flow rate of the second stream; recycling the first stream to the first reactor; passing the second stream, at a temperature of 20°–55° C. at a liquid space velocity of 0.1–50 1/hour and at a pressure of 1–50 atmospheres, through a second reactor filled with strong acid type cation exchange resin particles having an average particle diameter of 0.2–10 mm; passing the stream from the second reactor through a fixed bed filled with a water-insoluble solid particulate acid neutralizing agent having an average particle diameter of 0.1–10 mm at a temperature of about 0°–55° C.; passing the resulting reaction mixture into a flashing tower whereby the unreacted hydrocarbon is removed; and recovering a mixture containing MTBE from the bottom of the flashing tower.

12 Claims, 1 Drawing Figure

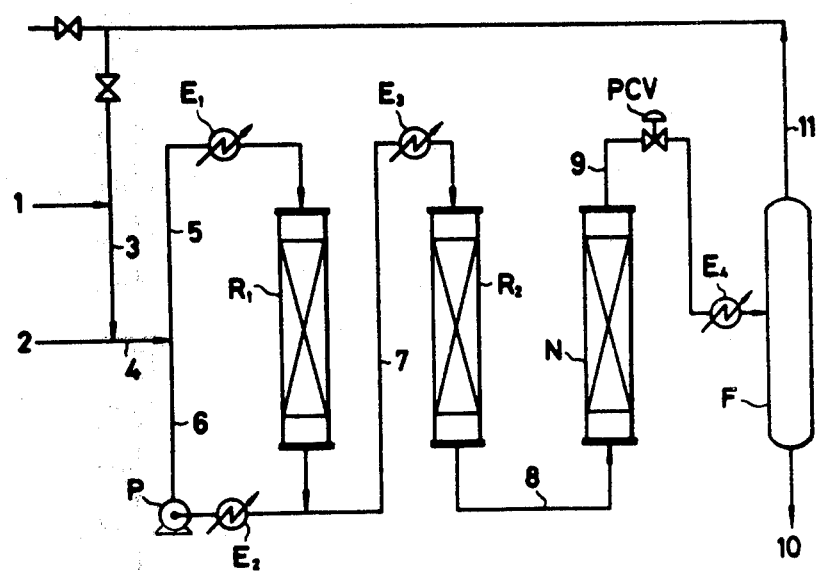

PROCESS FOR PREPARING METHYL TERTIARY-BUTYL ETHER

BACKGROUND OF THE INVENTION

1. Field of the Invention

The present invention relates to a process for preparing methyl tertiary-butyl ether (hereinafter referred to as "MTBE") by the continuous reaction of an isobutylene hydrocarbon with methanol in the presence of a catalyst, giving a high yield.

2. Brief Description of the Prior Art

In recent years, pollution resulting from lead present in exhaust gases from internal combustion engines has become a big problem. Accordingly, regular type gasolines are entirely leadless at the present time, and premium type gasolines will sooner or later be made leadless. However, in order to make gasoline leadless without a big change in the mixing ratio of the base gasolines while maintaining the octane number of conventional gasolines, it is necessary to add an agent for increasing the octane number.

A number of agents for increasing octane number are already known. Among them, ethers having a branched chain type alkyl group were disclosed in the Third World Petroleum Congress, Sec. M, 397 (1951). It is known that, for example, methyl tertiary-butyl ether (MTBE), ethyl tertiary-butyl ether, and isopropyl tertiary-butyl ether have extremely high octane numbers.

It is known that MTBE can be prepared by the reaction of methanol and isobutylene in the presence of an acid catalyst. In particular, some processes have been proposed in which a strong acid type cation exchange resin is employed as the catalyst (for example, Japanese Patent Publication No. 34,803/1973, Published unexamined Japanese Patent Application Nos. 61,109/1974 and 58,006/1975 and U.S. Pat. No. 2,480,940). However, these conventional processes permit the extraction of acidic materials into the mixture of reaction products from the strong acid type cation exchange resins used during the reaction, so that a heating procedure is required in the distillation step in which the reaction products are separated. This heating procedure, however, produces undesirable effects in that a considerable degree of a reverse reaction from the MTBE product to the methanol and isobutylene occurs, thereby resulting in a decrease in the yield of the MTBE because of the presence of the tertiary carbon atom in the MTBE. Furthermore, products which contain acidic materials cannot be added as they are to fuel gasolines.

The present inventors have invented and already applied for a patent on an invention for the continuous process for preparing a tertiary alkyl ether from a lower primary alcohol and a tertiary olefin on an industrial scale and with good yield by carrying out the flashing and distillation operations after removal of the undesirable acidic materials from the reaction product mixtures by means of a solid particulate acid neutralizing agent (Japanese Patent Application No. 140,479/1976).

Furthermore, the present inventors have invented and already applied for another patent on an invention directed to a process which comprises reacting an olefin with a lower alcohol in an excessive amount with respect to the olefin used, removing the acidic materials by means of a solid particulate acid neutralizing agent, then removing the unreacted hydrocarbon by means of a flashing procedure, further distilling the distilled reaction mixtures to provide an azeotropic mixture of MTBE and methanol at the top of a distillation tower, recycling the azeotropic mixture to the first reactor where the olefin is reacted with the lower alcohol, and providing a high purity MTBE at the bottom of the distillation tower (Japanese Patent Application No. 123,154/1977).

SUMMARY OF THE INVENTION

It is an object of the present invention to provide a process for continuously preparing methyl tertiary-butyl ether with high yield.

It is another object of the present invention to provide a process for continuously preparing methyl tertiarybutyl ether in which one portion of the reaction mixture obtained by the reaction of isobutylene with methanol is recycled to the first reactor where the reaction is carried out, and the rest of the reaction mixture is passed to the second reactor where the conversion to MTBE is enhanced.

It is a further object of the present invention to provide a process for the continuous manufacture of methyl tertiary-butyl ether in which the reaction between isobutylene and methanol is carried out by a two-step procedure involving two reactors each of which is filled with strong acid type cation exchange resins having different physical properties.

BRIEF DESCRIPTION OF THE DRAWING

The FIGURE is a flow chart illustrating one embodiment of the present invention.

DETAILED DESCRIPTION OF THE INVENTION

The present invention relates to a process for preparing MTBE from an isobutylene-containing hydrocarbon mixture and methanol by two-step procedures under particular reaction conditions. More specifically, the process is conccerned with a continuous process for manufacturing MTBE which comprises reacting an isobutylene-containing hydrocarbon with methanol by continuously passing the isobutylene hydrocarbon and methanol, in a molar ratio of isobutylene to methanol of 1/0.6–1.4 at a temperature of 60°–100° C. with a liquid space velocity of 0.1–50 (1/hour) and at a pressure of 1–50 atmospheres, through a first reactor filled with strong acid type cation exchange resin particles having an average particle diameter of 0.2–10 mm; dividing the mixture of reaction products into two streams in which the flow rate of the first stream is 3 to 15 times (by weight) the flow rate of the second stream; recycling the first stream to the first reactor filled with the aforementioned cation exchange resin; passing the second stream, at a temperature of 20°–55° C. with a liquid space velocity of 0.1–50 (1/hour) and at a pressure of 1–50 atmospheres, through a second reactor filled with strong acid type cation exchange resin particles having an average particle diameter of 0.2–10 mm; passing the stream from the second reactor through a fixed bed filled with a water-insoluble solid particulate acid neutralizing agent having an average particle diameter of 0.1–10 mm at a temperature of 0°–55° C.; passing the resulting reaction mixture into a distillation tower whereby the unreacted hydrocarbon is removed; and collecting a mixture containing MTBE from the bottom of the flashing tower.

The raw materials to be used in the present invention are an isobutylene hydrocarbon and methanol. Although isobutylene of high purity grade may be employed as the isobutylene hydrocarbon, a hydrocarbon mixture containing isobutylene may also be used. That is, the mixture may contain, in addition to isobutylene, n-butane, isobutane, butene-1, butene-2, butadiene or the like. For example, $C_4$ hydrocarbon fractions obtainable by cracking, steam decomposition or catalytic cracking of petroleum (usually containing 15 to 50 percent by weight of isobutylene) may be effectively employed. Methanol which is commercially available may be used; however, methanol containing less than about 1 percent by weight of water is preferable.

In accordance with the present invention, the employment of a solvent is not necessary. However, when a solvent is employed, a solvent which is inert to the reeaction may be used in an amount less than about 10 times the reactant. When a $C_4$ hydrocarbon mixture is used as the raw material, the $C_4$ hydrocarbons other than the isobutylene contained therein may be regarded as solvent.

The isobutylene hydrocarbon and methanol may be introduced separately or as a mixture, after being preheated close to the reaction temperature, to the reactor which is filled with a strong acid type cation exchange resin.

The present invention is characterized by the application of two reactors wherein the first reactor, having a higher reaction temperature than that of the second reactor, is intended to raise the space time yield of the reaction product while impairing the chemical equilibrium to some extent, and the second reactor, where the reaction temperature is set lower than that of the first reactor, is intended to raise the overall conversion due to the fact that the chemical equilibrium favors the reaction product side while impairing the reaction velocity.

In accordance with the present invention, there is adopted a process in which the reaction mixture obtained by the reaction of methanol and isobutylene in the first reactor which is filled with a strong acid type cation exchange resin is divided into two streams, the first stream being recycled to the first reactor and the second stream being passed to the second reactor. The flow rate of the first stream to be recycled to the first reactor is from 3 to 15 times, and preferably from 5 to 10 times, the flow rate of the second stream to be passed into the second reactor.

The reasons for adopting the recycling system in the present invention are based on the following grounds. The reaction between methanol and isobutylene according to the present invention is an exothermic reaction, and 95 percent of the heat produced in the full course of the reaction is in the first reactor. Accordingly, in the case where no recycling system is applied, the difference in temperature between the inlet and the outlet of the first reactor will be very great and, in particular, the temperature at or near the outlet will be very high. Such high temperatures may increase side effects and deteriorate catalysts to be employed, so these temperatures should be avoided. Accordingly, in this case, the reactor should be equipped with a special cooling device or the like. However, due to poor heat conductivity of the ion exchange resins in the reactor, the cooling device must be of a multitubular cooler type. The application of this system, however, requires a complicated procedure for replacement of the catalyst. Moreover, even in this case, localized high temperature spots my occasionally occur in the exchange resin, and this is disadvantageous. In the case where the recycling system is applied, however, the temperatures throughout the reaction bed may be maintained substantially uniform.

The stream of reaction products from the first reactor is led to the second stream. In the second reactor, a piston flow system may be applicable apart from the recycling system because the second reactor accounts for only approximately 5 percent of the heat produced in the entire course of the reaction, and the difference in temperature between the inlet and the outlet is not great.

In accordance with the present invention, the reaction temperature in the first reactor may range from 60° C. to 100° C., while the reaction temperature in the second reactor may range from 20° C. to 55° C. When the reaction temperature in the first reactor is below 60° C., the reaction velocity is too slow to provide a sufficient space time yield. When it is above 100° C., it is undesirable because side effects, such as a low molecular polymerization of isobutylene, may be increased. The preferred reaction temperature in the first reactor is between 65° C. and 80° C.

When the reaction temperature in the second reactor is below 20°, the reaction may not proceed well. Temperatures higher than 55° C., on the other hand, may not allow a high equilibrium conversion, for example, higher than 96 percent, because the equilibrium value will not favor the product side. The preferred reaction temperature in the second reactor is in the range of 30° C. to 50° C.

The pressures to be used in the present invention are in the range from 1 to 50 atmospheres, preferably from 5 to 30 atmospheres in both the first and the second reactor. The reaction cannot be adequately accomplished under a pressure lower than 1 atm, and since a pressure higher than 50 atm, requires that the reactors and their accessories must be made firmly resistant to pressure, it is industrially disadvantageous.

Isobutylene and methanol in the raw material system to be supplied to the first reactor are in the molar ratio of isobutylene to methanol of 1/0.6–1.4, preferably 1/0.75–1.2. The raw material system referred to herein means the raw materials which are supplied to the first reactor and excludes the stream to be recycled to the first reactor. If the supply of the raw material system has a molar ratio lower than 0.6, the amount of isobutylene exceeds that of methanol resulting in an increase in unreacted isobutylene and isobutylene dimers. In particular, when butane-butene fractions obtainable from naphtha decomposition are used as the raw materials for isobutylene, a lower molar ratio is undesirable because the reaction ratio of isobutylene must be raised as high as posible so that $C_4'$-1, $C_4'$-2 or the like in the unreacted butane-butene fractions after the reaction may be utilized.

If the isobutylene to methanol molar ratio is above 1.4 the amount of unreacted methanol will be so large that the amount of methanol in the mixture containing the collected MTBE is increased or, if a technique is adopted which recycles an azeotropic mixture of MTBE and methanol to the raw material system, the amount of the azeotropic mixture will be large whereby, in both cases, the amount of the MTBE product is decreased. That is, the composition of the azeotropes is in the MTBE to methanol ratio of 85:15 (by weight); accordingly, the more the amount of unreacted methanol grows, the more the amount of MTBE in the azeotropic mixture grows. Therefore, the amount of the MTBE product to be recovered from the bottom of the distillation tower will be low. The amount of the MTBE in the azeotropic mixture to be recycled to the raw material system must be, at the most, 50 percent of the MTBE amount produced in the first reactor, and a larger amount is economically undesirable.

The strong acid type cation exchange resin to be used in the present invention is an cationic exchange resin having a strong acidity and includes as representatives, a styrenic sulfonic acid type resin, a phenol sulfonic acid type resin or the like. A styrenic sulfonic acid type ion exchange resin may be prepared by copolymerizing styrene and a poly-unsaturated compound such as divinyl benzene and then sulfonating the resulting resin. Resins of this type may be represented by the following general formula:

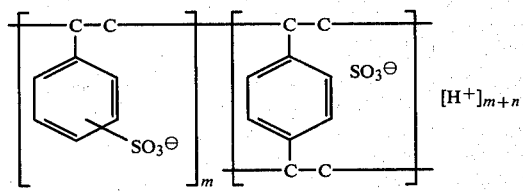

A phenol sulfonic acid type resin may be condensate of phenol sulfonic acid with formaldehyde and may be represented by the following general formula:

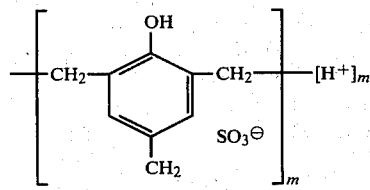

(where m and n are integers).

The above-mentioned strong acid type cation exchange resin is used as a catalyst in the present invention and may be a spherical or cylindrical particles having an average particle diameter of 0.2–10 mm.

The catalyst particles are supplied to the first and the second cylindrical reactors with a pressure-resistant construction, and constitute a fixed bed. The size of the fixed bed is not particularly limited, but it is usually from 0.2 meter to 20 meters high.

The aforementioned methanol and isobutylene may be continuously supplied from the top end or the bottom end of the fixed bed, preferably the top end. The amount to be supplied has a liquid space velocity $$\left( \frac{m^3}{m^3} \times \frac{1}{hr} = \frac{1}{hr} \right)$$

of 0.1 to 50, preferably 0.5 to 15 (1/hr). The liquid space velocity for the first reactor may be represented by the total volume (m³) of a stream to be supplied to the first reactor (excluding the stream to be recycled to the first reactor) per m³ of catalyst per hour under the conditions of 20° C. and 2.5 Kg/cm³. With respect to the second reactor, the liquid space velocity may be represented by the volume (m³) of a stream passing through the second reactor per hour (hr) per m³ of catalyst under the same conditions as in the first reactor.

When the amounts of the reactants to be supplied as the raw materials are smaller than 0.1 (1/hour), the reaction can proceed well, but the amount of the product will be so small that it is industrially undesirable, and decomposition of the reaction product increases. When amount of the reactants exceeds 50 (1/hour), a sufficient reaction may not be achieved. This will require more purification than is usually required and consequently is disadvantageous.

An inert solvent, particularly an inert hydrocarbon solvent, may be used. For example, $C_4$ hydrocarbon fractions obtainable by naphtha distillation, or butane-butene fractions obtained by separation and removal of butadiene from the above-mentioned $C_4$ hydrocarbon fractions, may be used as raw materials for isobutylene.

In accordance with the present invention, the MTBE may be prepared with high yield and with good selectivity by first converting about 90 percent of the raw materials to MTBE in the first reactor and then reacting a majority of the remaining unreacted raw materials in the second reactor. However, this procedure presents an undesirable effect in that small amounts of substances having a strong acidity are continuously extracted from the strong acid type cation exchange resins used as the catalysts and are mixed into the reaction mixture. If the reaction mixture in which such acidic substances are mixed were supplied, as is, to the subsequent step of separating the unreacted gases and then subjected to the distillation operation which usually accompanies the heating procedure, the main reaction product would be decomposed by a reverse reaction, thereby resulting in a decreased yield. In addition, corrosion of the apparatus would occur.

Accordingly, these strongly acidic substances must be removed. One idea would be a procedure for neutralizing the acidic substances by the addition of an aqueous solution of a strongly basic substance such as sodium hydroxide, calcium oxide or calcium hydroxide. However, this procedure presents the difficulties of separating the salts produced by neutralization and of controlling the amount of the added basic substance due to a comparatively wide variation in the concentration of the acid substance depending on the kind of catalyst used, the reaction temperature, the amounts of the raw materials, the reaction time, and the like. When the amount of the basic substance is too small, the acidic substance cannot be completely removed, so that the aforementioned difficulties and drawbacks still remain unsolved. When the amount of the basic substance is too large, the subsequent step of separating the unreacted gases shoul be carried out under conditions required for handling strongly alkaline substances. Accordingly, procedures for washing the product with water, distilling the product, or the like are required before mixing with fuel for internal combustion engines, and this is extremely undesirable.

If sodium hydroxide, calcium oxide or the like were employed in solid form, these solids would be eluted, and the difficulties mentioned hereinbefore would occur.

Another idea would be to remove the acidic substances by means of an adsorbent such as activated carbon or the like. However, since its capacity of adsorption is small, it has some drawbacks in that its ability to absorb the acidic substances may be decreased in a remarkable extent when the concentration of the acidic substances is low.

In order to solve these difficulties and drawbacks and allow methanol and isobutyl to react extremely effectively and continuously, one of the characters features of the present invention is that the reaction mixture from the second reactor is passed through a fixed bed filling with a water-insoluble solid particulate acid neutralizing agent having an average particle diameter of 0.1–10 mm, and consequently the former is brought into contact with the latter. In carrying out this procedure, the difficulties and drawbacks mentioned hereinabove are solved. The water-insoluble solid particulate acid neutralizing agent referred to herein is inorganic solid particulate material having an extremely small solubility in water, usually a water solubility of smaller than about 0.1 gram per 100 grams of water, and an active acid neutralization point of greater than 1.0 millimole/gram.

The active acid neutralization point referred to herein is determined by calculating the millimoles (m moles) of removable $H_2SO_4$ per gram of the above solid material remaining in an aqueous solution prepared by the addition of a given amount of the solid material to a 1 wt.% aqueous $H_2SO_4$ solution and the removal of the solid material from the solution after standing for 10 hours at 50° C.

Examples of water-insoluble solid particulate acid neutralizing agents which may usually be used in the present invention include magnesium oxide, alumina, silica, silica alumina, complex oxides of Mg and Al and hydrates thereof, and complex oxides of Mg and/or Al with at least one element selected from a group consisting of Na, K, C, Si, Ca, Ba and Sr and hydrates thereof. For example, MgO, $MgO.mH_2O$ (m=0–0.5), $Al_2O_3$, hydrotalcite ($6MgO.Al_2O_3.CO_2.12H_2O$), $Al_2O_3.mSiO_2.nH_2O$ (m=0.5–3, n=1–6), $Al_2O_3.nH_2O$, $2.5MgOAl_2O_3.nH_2O$, $Na_2O.Al_2O_3.nH_2O$, and $2MgO.6SiO_2.nH_2O$ (in each case, n=1–6) may be employed. Among these, hydrotalcite and MgO are preferable in the present invention. The hydrotalcite referred to herein is usually in the molar ratio of magnesium to aluminium of 3:1. Hydrotalcites having similar compositions, but having widely varying magnesium-to-aluminium molar ratios may be synthetically prepared depending upon the process; however, there are those having magnesium-to-aluminium molar ratios ranging from 1–10:1 which exhibit X-ray diffraction peaks peculiar to hydrotalcites with magnesium-to-aluminium molar ratios of 3:1. Accordingly, hydrotalcite having a magnesium-to-aluminium molar ratio between 1–10:1 and exhibiting such peaks may be effectively employed in accordance with the present invention.

The solid particulate acid neutralizing agent according to the present invention may fill a container as a fixed bed in spherical, flaky or cylindrical form having an average particle diameter 0.1–10 mm.

The reaction mixture is continuously passed through the fixed bed at a temperature of 0°–55° C., preferably 20°–50° C. When the temperature is lower than 0° C., the acidic materials may not be sufficiently removed, and it is disadvantageous because the reaction mixture from the reactor must be heated so that a loss on heat may be caused. A temperature higher than 55° C. may require the reaction mixture from the reaction to be cooled so that it is disadvantageous that a heat loss may be caused. The preferred temperature is around the reaction temperature. That is, it is preferred that reaction mixture be led to the bed filled with the acid neutralizing agent through a line between the reactor outlet and the inlet of the above bed, the line being allowed to cool under ambient temperature. The amount of the reaction mixture to be passed through the fixed bed is usually at a liquid space velocity of 0.1–20 (l/hour).

In accordance with the present invention, the reaction mixture is then passed into a distillation tower and there subjected to the separation step. The flashing tower is usually of a multistage type and separates and removes the unreacted hydrocarbons, i.e., the unreacted isobutylene and other hydrocarbons mixed with the isobutylene hydrocarbon from the tower top. Two or three flashing towers may be connected in series and used as one multistage. The separated isobutylene may be liquified and recycled to the first reactor.

A mixture containing MTBE is recovered from the bottom of the flashing tower. This mixture contains MTBE as the major ingredient and a small amount of unreacted methanol. The MTBE which is obtained by the process of the present invention may be added intact to a fuel for internal combustion engines.

When the molar ratio of methanol in the raw material system is high, the methanol content in the MTBE-containing mixture from the bottom of the flashing tower will also be high. Accordingly, when it is necessary to reduce the methanol content in the reaction mixture to as low a value as possible, the reaction mixture may be distilled in a distillation tower so that an azeotropic mixture of MTBE and methanol is distilled at the tower top and high purity MTBE is effectively recovered from the tower bottom. The recycling of such an azeotropic mixture to the raw material system may permit an effective utilization of methanol. Where it is not necessary to recycle the azeotropic mixture to the raw material system, the washing of the azeotropic mixture with water or other solvents can achieve the separation of MTBE and methanol.

The process in accordance with the present invention will be described in more detail with reference to the drawing illustrating one embodiment of the process of the present invention.

Referring now to the drawings, the raw material isobutylene is charged through a line 1 and the raw methanol through a line 2. If necessary, the unreacted isobutylene which is recovered is recycled to the raw material system through a line 11.

The raw material fluid is led through lines 3 and 5 to a heater $E_1$ where it is heated to a predetermined temperature and then to a reactor $R_1$ provided with a fixed bed (not shown) filled with strong acid type cation exchange resin particles. The fluid discharged from the reactor $R_1$ is divided into two streams. One stream is led through line 6 by means of a recycling pump P, after being cooled by means of a cooler $E_2$, to the line 5 where it is combined with fresh raw material fluid from the line 4 and recycled through the line 5 to the rector $R_1$. The other stream is led through a line 7 to a heat exchanger $E_3$ where the stream is heated to a predetermined temperature and then fed into a reactor $R_2$ provided with a fixed bed which is filled with strong acid type cation exchange resin particles. The fluid discharged from the reactor $R_2$ is passed through a line 8 to a neutralization tower N having a fixed bed filled with a water-insoluble solid particulate acid neutralizing agent. The pressures in the reactors $R_1$, $R_2$ and the neutralization tower N are set by means of a pressure control valve (PCV) to predetermined levels. The fluid discharged from the neutralization tower N is led, after the pressure is reduced, through a line 9 to a heat exchanger $E_4$ (heater) where the temperature is controlled, and then led to the distillation tower F. The hydrocarbon mixture containing unreacted isobutylene is discharged through line 11 out of the top of the distillation tower F and, when reused, combined with the raw material isobutylene in the line 1 after being liquefied. The MTBE-containing mixture is recovered through line 10 from the bottom of the flashing tower F.

The following examples further illustrate the characteristic features of the present invention.

EXAMPLE 1

The reactors $R_1$, $R_2$ were filled with 90 liters of styrene type ion exchange resin (Rohm and Haas, Co.; Amberlist-15, average particle diameter, 0.5 mm), and the neutralization tower N was filled with 50 liters of hydrotalcite ($6MgO.Al_2O_3.CO_2.12H_2O$, average particle diameter, 0.7 mm). Isobutylene of 99% purity was fed through line 1 at a stream velocity of 118.7 kg per hour (2.12 kg mole/hour), and methanol of 99% purity was fed through line 2 at a stream velocity of 70.0 kg. per hour (2.19 kg. mole/hour). The liquid space velocities of the raw materials were each 3.2 (l/hour), and the pressure was held at 15 kg/cm$^2$ G by means of the PCV. One stream of the fluid from the first reactor was led through the line 6 to line 5 where the fresh raw materials, isobutylene and methanol, were combined with the stream and then fed through line 5 to the reactor $R_1$. The reactor $R_1$ was controlled by means of the heat exchange $E_1$ to be at an inlet temperature of 70° C., and the amount of the stream in line 6 was regulated to be 7 times the amount of the raw materials in line 4 by means of the recycling pump P. The amount of the stream passing through line 7 from the reactor $R_1$ was 188.7 kg/hour, and the composition thereof was 90.0 wt.% of the reaction product, 5.6 wt.% of unreacted isobutylene, and 4.4 wt.% of unreacted mathanol. The fluid was then fed through line 7 to the reactor $R_2$ where the inlet temperature was regulated to be 40° C. by means of the heat exchanger $E_3$. The fluid discharged from the reactor $R_2$ had a composition of 96.1 wt.% of MTBE, 1.7 wt.% of unreacted isobutylene, and 2.2 wt.% of unreacted methanol. The acid concentration of the fluid was $3.0 \times 10^{-4}$ eq/liter. This fluid was fed through line 8 to the neutralization tower N. The inlet temperature of the tower N was 45° C. The acid concentration of the liquid discharged from the neutralization tower N was $1.5 \times 10^{-7}$ eq/liter. The fluid then passed through the line 9 to the distillation tower where the unreacted isobutylene was separated. The product MTBE of 98.0% purity was discharged in at a stream velocity of 185.2 kg./hour through the line 10 from the bottom of the distillation tower.

EXAMPLE 2

The reactors $R_1$ and $R_2$ were filled with a catalyst obtained by the polymerization of styrene containing about 14% of divinyl benzene and the sulfonation of 90 liters of the resulting resin having particle diameters of 20–50 mesh. Isobutylene (purity, 99%) was fed through the line 1 at a stream velocity of 100.8 kg/hour (1.80 kg mole/hour), and methanol (purity, 99%) was fed through the line 2 at a stream velocity of 64.0 kg/hour (2.0 kg mole/hour). The liquid space velocities of the raw materials were each 2.8 (l/hour). The inlet temperatures of the reactors $R_1$ and $R_2$ were regulated to be 70° C. and 35° C., respectively, by means of the heat exchangers $E_1$ and $E_3$. The inlet temperature of the neutralization tower N was 32° C. Except as above, the procedure of Example 1 was repeated. The fluid passed through the line 7 had a composition of 90.2 wt.% of MTBE, 3.8 wt.% of unreacted isobutylene, and 6.0 wt.% of unreacted methanol. The fluid passed through the line 9 into the distillation tower F had a composition of 95.1 wt/% of MTBE, 0.7 wt.% of isobutylene, and 4.2 wt.% of methanol, and an acid concentration of $2.8 \times 10^{-7}$ eq/liter. The stream from the bottom of the distillation tower F through the line 10 was discharged at the rate of 163.6 kg/hour with some methanol.

EXAMPLE 3

The reactor $R_1$ was filled with 90 liters of styrene type anion exchange resin (Rohm and Haas, Co.; Amberlite IR-121 with H+ replacement; particle diameter, 0.6 mm) as the catalyst. The $C_4$ fractions containing 40% isobutylene were fed through the line 1 at a stream velocity of 147.0 kg/hour (isobutylene, 1.05 kg mole/hour), and methanol (99% purity) was fed through the line 2 at a stream velocity of 32.0 kg.hour (1.00 kg mole/hour). The procedure of Example 1 was repeated with the exception that the inlet temperatures of the reactors $R_1$ and $R_2$ were regulated to be 73° C. and 37° C. by means of the heat exchangers $E_1$ and $E_3$, respectively. The respective outlet temperatures were 83° C. and 45° C. The inlet temperature of the neutralization tower N was 42° C. The stream passing through the line 7 had a composition of 43.3 wt.% of MTBE, 54.6 wt.% of $C_4$ fractions, 2.1 wt.% of methanol. The stream passing through the line 9 into the distillation tower F had the composition: MTBE, 46.7 wt.%; $C_4$ fractions, 52.4 wt.%; and methanol, 0.9 wt.%; and the acid concentration was $3.0 \times 10^{-7}$ eq/liter. The product MTBE of 98.1% purity was obtained through the line 10 from the bottom of the distillation tower F at a stream velocity of 85.2 kg/hour. The only impurity was methanol.

What is claimed is:

1. A process for continuously preparing methyl tertiary-butyl ether which comprises reacting an isobutylene-containing hydrocarbon with methanol by continuously passing the isobutylene and methanol, in a molar ratio of isobutylene to methanol of 1/0.6–1.4 at a temperature of 60° to 100° C. with a liquid space velocity of 0.1 to 50 l/hour and at a pressure of 1 to 50 atmospheres, through a first reactor filled with strong acid type cation exchange resin particles having an average particle diameter of 0.2 to 10 mm; dividing the mixture of reaction products into two streams, the flow rate of the first stream being 3 to 15 times the flow rate of the second stream; recycling the first stream to the first reactor; passing the second stream, at a temperature of 20° to 55° C. with a liquid space velocity of 0.1 to 50 l/hour and at a pressure of 1 to 50 atmospheres, through a second reactor filled with strong acid type cation exchange resin particles having an average particle diameter of 0.2 to 10 mm; passing the stream from the second reactor through a fixed bed filled with a water-insoluble solid particulate acid neutralizing agent having an average particle diameter of 0.1 to 10 mm at a temperature of 0° to 55° C.; passing the resulting reaction mixture into a distillation tower whereby the unreacted hydrocarbon is removed; and recovering a mixture containing methyl tertiary-butyl ether from the bottom of the distillation tower.

2. A process according to claim 1, wherein the flow rate of the first stream to be recycled to the first reactor is 5 to 10 times the flow rate of the second stream to be led to the second reactor.

3. A process according to claim 1, wherein the strong acid type cation exchange resin is styrenic sulfonic acid type cation exchange resin or phenol sulfonic acid type cation exchange resin.

4. A process according to claim 1, wherein the isobutylene-to-methanol molar ratio is in the range of 1:0.75 to 1:1.2.

5. A process according to claim 1, wherein the liquid space velocity is in the range of 0.5 to 15 l/hour.

6. A process according to claim 1, wherein the pressure at the first reactor and the second reactor are in the range of 5 to 30 atmospheres.

7. A process according to claim 1, wherein the reaction temperature in the first reactor is in the range of 65° C. to 80° C. and the reaction temperature in the second reactor is in the range of 30° C. to 50° C.

8. A process according to claim 1, wherein the water-insoluble solid particulate acid neutralizing agent is hydrotalcite, magnesium oxide, alumina, silica, silica alumina, a complex oxide containing magnesium and aluminium or a hydrate thereof, or a complex oxide containing magnesium and/or aluminium with at least one of sodium, potassium, carbon, silicon, calcium, barium and strontium or a hydrate thereof.

9. A process according to claim 8, wherein the acid neutralizing agent has an average particle diameter in the range of about 0.1 to about 10 mm.

10. A process according to claim 1, wherein the reaction mixture is continuously passed through the fixed bed of the solid particulate acid neutralizing agent at a temperature between 20° and 50° C.

11. A process according to claim 10, wherein the reaction mixture is passed at a liquid space velocity in the range of 0.1 to 20 l/hour.

12. A process according to claim 11, wherein the flow rate of the first stream to be recycled is 5–10 times the flow rate of the second stream to be led to the second reactor, wherein the strong acid cation exchange resin is a styrenic sulfonic acid type cation exchange resin or a phenol sulfonic acid type cation exchange resin, wherein the isobutylene to methanol molar ratio is in the range of 1:0.75 to 1:1.2, wherein the reaction temperature in the first reactor is in the range of 65° C. to 80° C. and the pressure is 5–30 atmospheres, wherein the reaction temperature in the second reactor is in the range of 30° C. to 50° C. and the pressure is 5–30 atmospheres, and wherein the water soluble solid particulate acid neutralizing acid is hydrotalcite having an average particle diameter in the range of about 0.1 to about 10 mm.

* * * * *